United States Patent [19]

Diamond et al.

[11] 4,060,635

[45] Nov. 29, 1977

[54] AMIDINOUREAS FOR TREATING DIARRHEA

[75] Inventors: Julius Diamond, Morris Plains, N.J.; George H. Douglas, Paoli, Pa.

[73] Assignee: William H. Rorer, Inc., Fort Washington, Pa.

[21] Appl. No.: 558,187

[22] Filed: Mar. 31, 1975

[51] Int. Cl.$^2$ .................... A61K 31/17; A61K 31/33; A61K 31/40; A61K 31/775
[52] U.S. Cl. .............................. 424/322; 260/553 R; 260/553 A; 424/244; 424/267; 424/274; 424/275; 424/285; 424/304; 424/311

[58] Field of Search ...................... 260/553 R, 553 A; 424/322, 304

[56] References Cited

U.S. PATENT DOCUMENTS

| | | | |
|---|---|---|---|
| 3,539,616 | 11/1970 | Walls | 260/465 |
| 3,784,582 | 1/1974 | Walls | 260/465 |

*Primary Examiner*—Frederick E. Waddell
*Attorney, Agent, or Firm*—James A. Nicholson; John C. Smith, Jr.

[57] ABSTRACT

A new class of chemical compounds and their process of preparation is described. These compounds have valuable properties as anti-diarrheal agents.

22 Claims, No Drawings

AMIDINOUREAS FOR TREATING DIARRHEA

SUMMARY OF INVENTION

This invention describes a new class of chemical compounds and process for their preparations. This invention also describes a new method for the treatment of diarrhea disorders. This invention further provides valuable pharmaceutical preparations which are effective for the treatment of diarrhea disorders. This invention describes a class of chemical compounds called amidinoureas and the same possess an effective degree of activity which is capable of producing anti-diarrhea properties in mammals.

BACKGROUND OF THE INVENTION

Diarrhea is widespread among the world's population. In certain diseases, this enteric disorder can be the cause of a high degree of morbidity and even mortality.

The narcotic analgesics remain in the drugs of choice for treatment of diarrhea and dysentery. This group of drugs, however, has serious disadvantages. They possess the narcotic properties of producing sleep as well as analgesia. They also have physical and psychological dependence liabilities. Morphine and codeine remain two outstanding examples of this group.

In 1957 a meperidine derivative, diphenoxylate, was introduced into therapeutic regimen of diarrhea control. This agent possesses morphine-like as well as anticholinergic properties, both of which may be responsible for its anti-diarrheal actions. Diphenoxylate, because of its narcotic properties, is capable of supporting morphine physical dependence in the monkey. Overdoses in children can lead to symptoms and fatalities that are characteristic of the narcotics, e.g. respiratory depression and reversal of morbidity with nalorphine.

Past attempts have failed to indicate that a chemical could be found that would have anti-diarrheal properties without addiction liability, however:

We have unexpectedly found potent anti-diarrheal agents;

We have unexpectedly found a class of chemical compounds which have anti-diarrheal properties without accompanying side effects which are common with these agents;

We have further unexpectedly found that amidinourea compounds are effective antidiarrheal agents having a minimum of side effects;

We have also unexpectedly found that administration of amidinoureas is a simple and effective method for the treatment of diarrhea disorders which does not have physical dependence capacity;

We have still further found effective anti-diarrheal compositions void of undesirable side effects and which have an amidinourea compound as the active ingredient.

DESCRIPTION AND PREFERRED EMBODIMENTS

This invention describes a novel class of chemical compounds of the formula

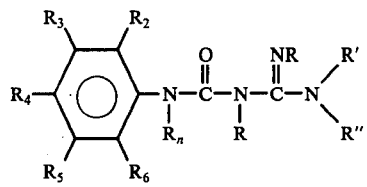

where:

$R_2$, $R_3$, $R_4$, $R_5$ and $R_6$ may be the same or different and are:
hydrogen,
halo,
loweralkyl,
haloloweralkyl,
nitro,
loweralkoxy,
hydroxy,
arloweralkoxy,
acyloxy,
cyano,
haloloweralkoxy or
loweralkylsulfonyl;
R is hydrogen or
loweralkyl;
R' and R" are hydrogen
alkyl
cycloalkyl or
aralkyl;
R' and R" together and may form a 5-7 atom ring which may include 0-2 hetero atoms of N, O or S;
$R_n$ is hydrogen or loweralkyl provided at least one of R, R' and R" is other than hydrogen; and
the non-toxic acid addition salts thereof.

Compounds of this invention which are preferred include those where:
$R_2$, $R_3$, $R_4$, $R_5$ and $R_6$ are hydrogen,
halo,
loweralkyl,
haloloweralkyl,
nitro,
hydroxy or
loweralkoxy; and
R and $R_n$ are hydrogen or loweralkyl and
R' and R" are hydrogen or alkyl; provided R, R' and R" are not all hydrogen at the same time.

The more preferred compounds of this invention include those where:
$R_2$ is hydrogen or loweralkyl;
$R_3$ and $R_5$ are hydrogen, hydroxy or loweralkoxy;
$R_4$ is hydrogen,
loweralkyl,
hydroxy,
loweralkoxy or
halo.
$R_6$ is hydrogen,
loweralkyl,
nitro,
alkoxy or
halo;
R and $R_n$ are hydrogen or loweralkyl; and
R' and R" are hydrogen or alkyl; provided R, R' and R" are not all hydrogen at the same time.

The most preferred compounds of this invention are those where:
$R_2$ is hydrogen, methyl or ethyl;

$R_3$ is hydrogen, hydroxy or methoxy;
$R_4$ is hydrogen, methyl, ethyl, hydroxy, methoxy, chloro or bromo;
$R_5$ is hydrogen, hydroxy or methoxy;
$R_6$ is hydrogen, methyl, ethyl, nitro, methoxy, ethoxy, chloro, bromo or fluoro;
R and $R_n$ are hydrogen, methyl or ethyl; and
R' and R" are hydrogen,
  methyl,
  ethyl,
  propyl,
  i-propyl,
  butyl,
  i-butyl,
  sec-butyl,
  t-butyl,
  pentyl,
  hexyl or;
  heptyl, provided R, R' and R" are not all hydrogen at the same time.

A special embodiment of this invention comprises compounds which have:
$R_2$-loweralkyl substitution;
$R_2$, $R_6$-diloweralkyl substitution;
$R_2$, $R_6$-loweralkyl, alkoxy substitution;
$R_2$, $R_6$-loweralkyl, halo substitution;
$R_2$, $R_6$-alkyl, nitro substitution;
$R_2$, $R_4$, $R_6$-triloweralkyl substitution, or
$R_2$, $R_4$, $R_6$-loweralkyl, dihalo substitution.

A further special embodiment of this invention comprises compounds which have:
$R_3$, $R_4$-hydroxy or alkoxy substitution;
$R_3$, $R_4$, $R_5$-hydroxy or alkoxy substitution.
$R_2$, $R_5$-dihalo substitution or
$R_2$, $R_6$-dihalo substitution.

A further special embodiment of this invention comprises compounds which have:
R, R' and R" as hydrogen or loweralkyl substitution provided all are not hydrogen at the same time; or
R and R' are hydrogen or loweralkyl and R" is an alkyl group from 3 to 7 carbon atoms.

This invention further describes a novel method for the treatment of diarrhea by the administration of a compound of the formula:

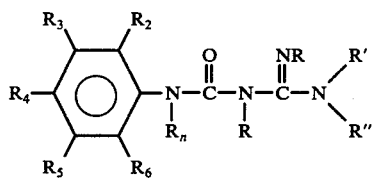

where:
$R_2$, $R_3$, $R_4$, $R_5$ and $R_6$ may be the same or different and are:
hydrogen,
halo,
loweralkyl,
haloloweralkyl,
nitro,
loweralkoxy,
hydroxy,
arloweralkoxy,
acyloxy,
cyano,
haloloweralkoxy or
loweralkylsulfonyl;

R and $R_n$ are hydrogen or loweralkyl;
R' and R" are hydrogen
  alkyl,
  cycloalkyl or
  aralkyl;
R' and R" together may form a 5–7 atom ring which may include 0–2 hetero atoms of N, O or S; and
the non-toxic acid addition salts thereof.

It is well known in the pharmacological arts that non-toxic acid addition salts of pharmacologically active amine compounds do not differ in activities from their free base. The salts merely provide a convenient solubility factor.

The amines of this invention may be readily converted to their non-toxic acid addition salts by customary methods in the art. The non-toxic salts of this invention are those salts the acid component of which is pharmacologically acceptable in the intended dosages; such salts would include those prepared from inorganic acids, organic acids, higher fatty acids, high molecular weight acids, etc., and include such as:
hydrochloric acid,
hydrobromic acid,
sulfuric acid,
nitric acid,
phosphoric acid,
methane sulfonic acid,
benzene sulfonic acid,
acetic acid,
propionic acid,
malic acid,
succinic acid,
glycolic acid,
lactic acid,
salicylic acid,
benzoic acid,
nicotinic acid,
phthalic acid,
stearic acid,
oleic acid,
abietic acid, etc.

The nomenclature applied to the compounds of this invention is as follows

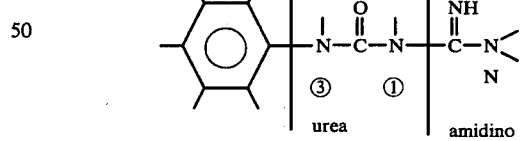

The term "loweralkyl" refers to an alkyl hydrocarbon group from 1 to 5 carbon atoms which may be straight chained or branched while "alkyl" refers to an alkyl hydrocarbon group which may have as many as ten carbon atoms.

The term "cycloalkyl" refers to a cycloalkyl group having 3–7 carbon atoms.

The "loweralkoxy" radical signifies an alkoxy group containing from 1 to about 5 carbon atoms which may be straight chained or branched.

The preferred "aryl" group is phenyl.

The preferred "aralkyl" groups are benzyl and phenethyl.

The preferred "haloloweralkyl" group is trifluoromethyl.

The preferred "haloloweralkoxy" group is trifluoromethoxy.

The compounds of this invention may be prepared by the following general synthesis:

Condensation of a substitutedphenyl isocyanate (prepared from an aniline and phosgene in the customary manner) with guanidine results in a 1-substitutedphenyl-3-amidinourea. The reaction is carried out in a polar medium using solvents such as dimethylformamide, tetrahydrofuran, etc. It is convenient to carry out the reaction by preparing the isocyanate in the reaction media and then forming guanidine in situ by hydrolyzing guanidine carbonate with base. Condensation of the isocyanate takes place when the guanidine forms and the amidinourea compound results.

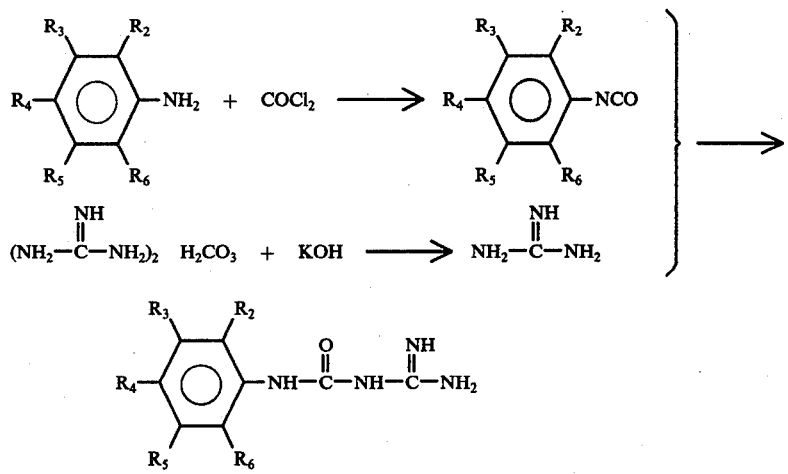

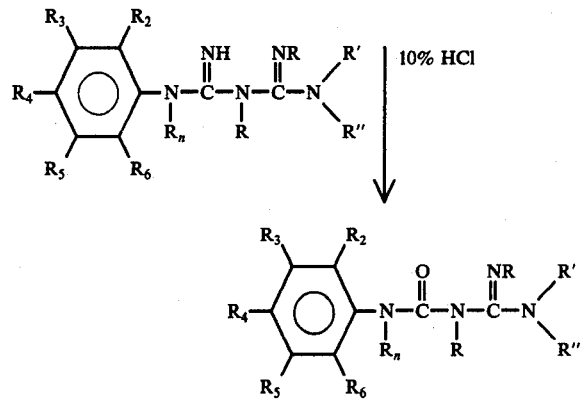

These compounds may also be prepared by degradation of the corresponding biguanide. When a 1-substitutedphenylbiguanide compound is hydrolyzed in acid at raised temperature then the resultant product is 1-substitutedphenyl-3-amidinourea. This reaction is preferably carried out using hydrochloric acid and the reaction time and reaction temperature will of course depend on the particular biguanide used and the concentration of the acid present. In general, the more concentrated acids will not require high temperatures or long periods of reaction time.

When it is desired to have R substitution at the N-3 the starting material of course will be an aniline having N-alkyl substitution. Reaction with phosgene results in the carbamoyl chloride which is then reacted with the guanidine to prepare the amidinourea.

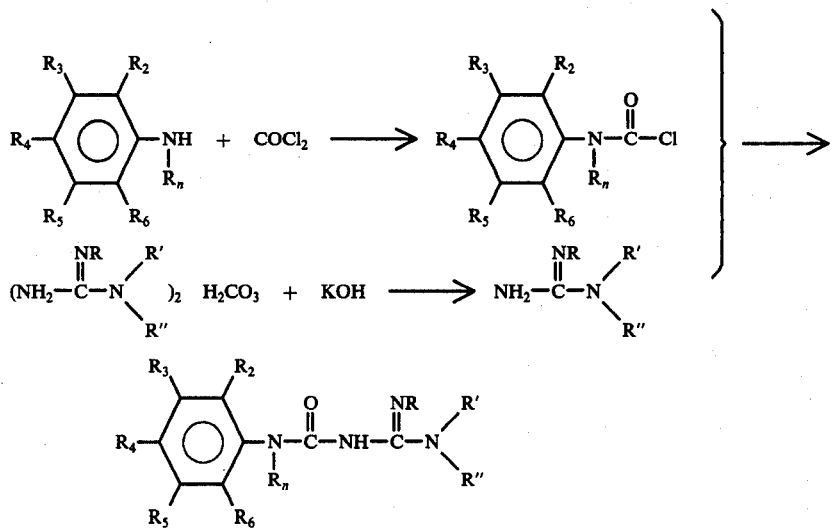

The starting anilines are either known, may be prepared by known techniques or reference to the preparation is shown. Thus, chlorination or bromination of an acetanilide or aniline may be carried out in acetic acid, or in the presence of a small amount of iodine dissolved in an inert solvent such as carbon tetrachloride. A solution of chlorine or bromine is then added while the temperature is held near 0° C. Iodination may also be carried out by known methods using iodine monochloride (Cl I).

Alkylation may be carried out on an acetanilide using an alkyl halide and aluminum chloride under Friedel-Crafts conditions to obtain desired alkyl substitution.

Nitration may be carried out using fuming nitric acid at about 0° C.

A nitro compound may be hydrogenated to the corresponding amine which may then be diazotized and heated in an alcohol medium to form the alkoxy compound.

An amino compound may also be diazotized to the diazonium fluoroborate which is then thermally decomposed to the fluoro compound.

Diazotization followed by a Sandmeyer type reaction may yield the bromo, chloro or iodo compound.

When an amino compound is diazotized followed by reaction with potassium ethylxanthate and then hydrolyzed, the mercapto compound results. This in turn may be alkylated to the alkylthio group which is then oxidized to the corresponding alkylsulfonyl substituent.

A chloro, bromo or iodo compound may also be reacted with trifluoromethyliodide and copper powder at about 150° C in dimethylformamide to obtain a trifluoromethyl compound [Tetrahedron Letters: 47, 4095 (1959)]. A halo compound may also be reacted with cuprous methanesulfinate in quinoline at about 150° C to obtain a methylsulfonyl compound.

When it is desired that the final product contain an hydroxy group, it is preferred that the starting aniline contain the corresponding acyloxy or aralkyloxy groups. These may be prepared in the usual fashion by acylating the starting hydroxy aniline compound with an acyl halide or anhydride in the presence of a tertiary amine or aralkylating with an aralkyl halide or sulfate. Of course the amine function would be protected in the customary manner. Hydrogenation to the desired hydroxy compound may then take place after the formation of the amidinourea. This may be accomplished with a metal catalyst (Pd/C, Pt etc.) in a polar medium (ethanol, THF, etc.), sodium in liquid ammonia etc. Thus, for example, the 3,4-dihydroxy amidinourea compound may be prepared from the corresponding 3,4-dibenzyloxyaniline. The hydroxy compounds may also be prepared by hydrolysis of the acyl or aralkoxy compounds with acid.

Reactions may also be carried out at other stages of synthesis depending on the substituents present and the substituents desired and various combinations of the foregoing reactions will be determined by one skilled in the art in order that the desired product results. Thus, a phenylamidinourea may be halogenated or nitrated as above, etc.

The biguanide starting materials are also either known, may be prepared by known procedures or may be prepared by the following general synthesis:

Condensation of cyanoguanidine and an aniline in the presence of an equimolar amount of a mineral acid results in the corresponding phenylbiguanide

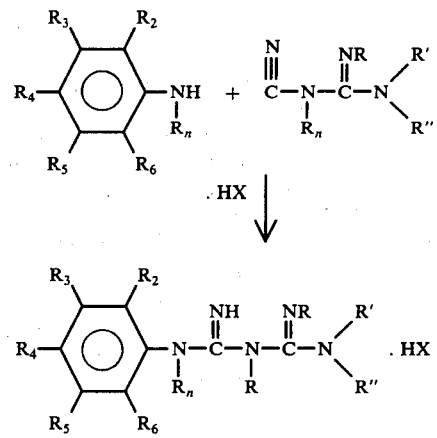

This reaction is preferably carried out on the aniline salt either in a polar medium or neat and using increased temperatures. The appropriately substituted product may be prepared by the reactions above when the same are also carried out on the biguanide or amidinourea.

The compounds described in this application are useful antidiarrheal agents. For these purposes they can be administered orally, parenterally or rectally. Administration by the oral route is preferred. Orally, these compounds may be administered in tablets, hard or soft capsules, aqueous or oily suspensions, dispersible powders or granules, emulsions, syrups or elixers. The optimum dosage, of course, will depend on the particular compound being used and the type and severity of the condition being treated. In any specific case the appropriate dosage selected will further depend on factors of the patient which may influence response to the drug; for example, general health, age, weight, etc. of the subject being treated.

Although the optimum quantities of the compounds of this invention to be used as anti-diarrheal agents will depend on the compound employed and the particular type of disease condition treated, oral dose levels of preferred compounds when administered to a mammal in dosages of 0.01 to 500 milligrams per kilogram of body weight per day are particularly useful. The preferred range is 0.05 to 200 mg/kg. Comparative dosages may be used in parenteral or rectal administration.

Compositions intended for oral use may be prepared according to methods known to the art for the manufacture of pharmaceutical compositions. Such compositions may contain one or more agents selected from the group consisting of sweetening agents, flavoring agents, coloring agents, preserving agents, etc. in order to provide a pharmaceutically elegant and palatable preparation.

Further the active amidinourea may be administered alone or in admixture with other agents having the same or different pharmacological properties.

The composition may contain such selected excipients such as inert diluents such as calcium carbonate, lactose, etc.; granulating and disintegrating agents such as maize starch, alginic acid, etc.; lubricating agents such as magnesium stearate, etc.; binding agents such as starch gelatin, etc.; suspending agents such as methylcellulose, vegetable oil, etc.; dispersing agents such as lecithin, etc.; thickening agents such as beeswax, hard paraffin, etc.; emulsifying agents such as naturally-occurring gums, etc.; non-irritating excipients such as cocoa butter, polyethylene glycols, etc.; and the like. Further, in formulating these compounds for every 100 parts by weight of the composition, there may be present between 5 and 95 parts by weight of the active ingredient. The dosage unit form will generally contain between 0.1 mg. and about 500 mg. of the active ingredients of this invention. The preferred unit dose is between 1 mg. and about 50 mg. The compositions may be taken 1-8 times daily depending on the dosage unit required.

Various tests can be carried out in animal models to show the ability of the amidinoureas of this invention to exhibit reactions that can be correlated with anti-diarrheal activity in humans. The following tests show the ability of the compounds of this invention to inhibit diarrhea in animals and are known to correlate well with anti-diarrheal activity in humans. These are considered to be standard tests used to determine anti-diarrhea properties. This correlation can be shown by the activities of compounds known to be clinically active. In view of the results of these tests, the amidinoureas of this invention can be considered to be anti-diarrheal agents.

1. Fecal output in rat: — The oral $ED_{50}$ (that dose which would be expected to reduce fecal output by 50%) is determined by a method described by Bass et al., 1972. Briefly, the method involves dosing the rats and collecting the fecal output over an 8 hour period (4 PM — 12 midnight) with the room darkened starting at 4:30 P.M.

Ref: — Bass, P., Kennedy, J. A. and Willy, J. N.: Measurement of fecal output in rats. Am. J. Dig. Dis. 10: 925–928, 1972.

2. Castor oil test in mice: — Groups of mice are orally dosed with test compound and half hour later all mice are given 0.3 ml. of castor oil. Three hours after castor oil administration, all mice are checked for diarrhea and the dose of testing compound which protected 50% of mice for diarrhea is the $ED_{50}$ dose. p 3. Castor oil test in rats: — The test is conducted according to Niermegeers et al. 1972. The rat is orally dosed with graded doses of test compound. One hour after dosing, each animal is challenged with 1 ml. of castor oil orally. Fecal output is examined 1, 2, 3, 4, 6, and 8 hours after castor oil. Absence of diarrhea is criterion of drug effectiveness.

Ref: - Niemegeers C. J. E., Lenaerts, F. M. and Janssen, P. A. J. Difenoxine, a potent, orally active and safe anti-diarrheal agent in rats. Arzneim-Forscth (Drug Res.) 22, 516–1518, 1972.

The following are detailed examples which show the properties of the compounds of this invention. They are to be construed as illustrations of said compounds and not as limitations thereof.

EXAMPLE 1

1-Amidino-3-(2,6-dimethylphenyl)urea

To 12.1 g (0.1 mole) of 2,6-dimethylaniline in 300 ml. of anhydrous benzene is added 325 ml. of 12.5% phosgene in benzene (0.395 mole). The reaction mixture is refluxed for 2 hours and the benzene is stripped off under reduced pressure to get rid of the phosgene and the residue purified by distillation. This is 2,6-dimethylphenylisocyanate and is then dissolved in 50 ml. of tetrahydrofuran and added dropwise to a heterogeneous mixture of 11.2 g. of potassium hydroxide and 18 g. of guanidine carbonate in 250 ml. tetrahydrofuran. This mixture is stirred for 8 hours and then 35 ml. of conc. hydrochloric acid is added followed by 40 ml. of conc. sodium hydroxide solution maintaining the mixture cool in a cold water bath. The mixture is next poured into 1500 ml. of water and the tetrahydrofuran is removed under diminished pressure. The mixture is extracted with ether which is then dried and evaporated to dryness to obtain 1-amidino-3-(2,6-dimethylphenyl)urea.

The hydrochloride is prepared by dissolving the free base in methanol and adding a methanolic hydrogen chloride solution to form the salt. The volume of the mixture is concentrated, ether added and 1-amidino-3-(2,6-dimethylphenyl)urea hydrochloride is filtered off.

When 2,6-dimethylaniline in the above procedure is replaced by the anilines of Table I, below, then the corresponding products of Table II, below, are prepared.

Table I 2-methyl-6-chloroaniline
2-methyl-6-fluoroaniline
2-methyl-6-bromoaniline
2-methyl-6-iodoaniline
2-methyl-6-methoxyaniline
2-methyl-6-ethoxyaniline
2-methyl-6-ethylaniline
2-methyl-6-propylaniline
2-methyl-6-i-propylaniline
2-methyl-6-butylaniline
2-methyl-6-cyanoaniline
2-methyl-6-trifluoromethylaniline
2-methyl-6-nitroaniline
2-methyl-6-methylsulfonylaniline
2-ethyl-6-chloroaniline
2-ethyl-6-fluoroaniline
2-ethyl-6-bromoaniline
2-ethyl-6-methoxyaniline
2-ethyl-6-ethoxyaniline
2,6-diethylaniline
2-ethyl-6-propylaniline
2-ethyl-6-trifluoromethylaniline
2-propyl-6-chloroaniline
2-propyl-6-fluoroaniline
2-propyl-6-bromoaniline
2-propyl-6-methoxyaniline
2-propyl-6-ethoxyaniline
2,6-dipropylaniline
2-i-propyl-6-chloroaniline
2-i-propyl-6-fluoroaniline
2-i-propyl-6-methoxyaniline
2-butyl-6-chloroaniline
2-methyl-3-chloroaniline
2-methyl-5-chloroaniline
2,4-dichloroaniline
2,5-dichloroaniline
2,6-dichloroaniline
2-chloro-3-methylaniline
2-chloro-4-methylaniline
2-chloro-5-methylaniline
2-chloro-5-fluoroaniline
2-chloro-5-bromoaniline
2-chloro-5-trifluoromethylaniline
2-fluoro-5-chloraniline
2-chloro-6-fluoroaniline
2,6-difluoroaniline
2-methylaniline
2-ethylaniline
2-propylaniline
4-trifluoromethoxyaniline 4-methylsulfonylaniline
4-trifluoromethylaniline
3,4-dimethoxyaniline
3,4,5-trimethoxyaniline
3,4-diacetyloxyaniline
3,4-dibenzyloxyaniline
3,4,5-tribenzyloxyaniline
3,4-diethoxyaniline
2,4-dimethylaniline
2,4-diethylaniline
2-methyl-4-ethylaniline
2-ethyl-4-methylaniline
2-methyl-4-chloroaniline
2-methyl-4-bromoaniline
2-methyl-4-fluoroaniline
2-ethyl-4-chloroaniline
2-ethyl-4-fluoroaniline
2-methyl-4-methoxyaniline
2-ethyl-4-methoxyaniline
2,4,6-trimethylaniline
2,4-dimethyl-6-ethylaniline
2,4-dimethyl-6-chloroaniline
2,4-dimethyl-6-bromoaniline
2,4-dimethyl-6-fluoroaniline
2,4-dimethyl-6-trifluoromethylaniline
2,4-dimethyl-6-nitroaniline
2,4-dimethyl-6-methoxyaniline
2,6-dimethyl-4-ethylaniline
2,6-dimethyl-4-chloroaniline
2,6-dimethyl-4-bromoaniline
2,6-dimethyl-4-fluoroaniline
2,6-dimethyl-4-methoxyaniline
2-methyl-4,6-dichloroaniline
2-methyl-4,6-difluoroaniline
2-methyl-4-fluoro-6-bromoaniline
2-methyl-4-fluoro-6-chloroaniline
2-methyl-4-bromo-6-chloroaniline
2-methyl-4-chloro-6-fluoroaniline
2-methyl-4-chloro-6-bromoaniline
2-methyl-4-methoxy-6-chloroaniline
2-methyl-4-ethyl-6-chloroaniline
2-methyl-4-chloro-6-trifluoromethylaniline
2-methyl-4-trifluoromethyl-6-chloroaniline
2-ethyl-4,6-dichloroaniline
2-ethyl-4,6-difluoroaniline
2-ethyl-4-fluoro-6-bromoaniline
2-ethyl-4-fluoro-6-chloroaniline
2-ethyl-4-bromo-6-chloroaniline
2-ethyl-4-chloro-6-fluoroaniline
2-ethyl-4-chloro-6-bromoaniline
2,6-diethyl-4-chloroaniline
2,6-diethyl-4-bromoaniline
2,6-diethyl-4-fluoroaniline
2,4-dimethyl-6-nitroaniline Table II 1-amidino-3-(2-methyl-6-chlorophenyl)urea
1-amidino-3-(2-methyl-6-fluorophenyl)urea
1-amidino-3-(2-methyl-6-bromophenyl)urea
1-amidino-3-(2-methyl-6-iodophenyl)urea
1-amidino-3-(2-methyl-6-methoxyphenyl)urea
1-amidino-3-(2-methyl-6-ethoxyphenyl)urea
1-amidino-3-(2-methyl-6-ethylphenyl)urea
1-amidino-3-(2-methyl-6-propylphenyl)urea
1-amidino-3-(2-methyl-6-i-propylphenyl)urea
1-amidino-3-(2-methyl-6-butylphenyl)urea
1-amidino-3-(2-methyl-6-cyano phenyl)urea
1-amidino-3-(2-methyl-6-trifluoromethylphenyl)urea
1-amidino-3-(2-methyl-6-nitrophenyl)urea
1-amidino-3-(2-methyl-6-methylsulfonylphenyl)urea
1-amidino-3-(2-ethyl-6-chlorophenyl)urea
1-amidino-3-(2-ethyl-6-fluorophenyl)urea
1-amidino-3-(2-ethyl-6-bromophenyl)urea
1-amidino-3-(2-ethyl-6-methoxyphenyl)urea
1-amidino-3-(2-ethyl-6-ethoxyphenyl)urea
1-amidino-3-(2,6-diethylphenyl)urea
1-amidino-3-(2-ethyl-6-propylphenyl)urea
1-amidino-3-(2-ethyl-6-trifluoromethylphenyl)urea
1-amidino-3-(2-propyl-6-chlorophenyl)urea
1-amidino-3-(2-propyl-6-fluorophenyl)urea
1-amidino-3-(2-propyl-6-bromophenyl)urea
1-amidino-3-(2-propyl-6-methoxyphenyl)urea
1-amidino-3-(2-propyl-6-ethoxyphenyl)urea
1-amidino-3-(2,6-dipropylphenyl)urea
1-amidino-3-(2-i-propyl-6-chlorophenyl)urea
1-amidino-3-(2-i-propyl-6-fluorophenyl)urea
1-amidino-3-(2-i-propyl-6-methoxyphenyl)urea
1-amidino-3-(2-butyl-6-chlorophenyl)urea
1-amidino-3-(2-methyl-3-chlorophenyl)urea
1-amidino-3-(2-methyl-5-chlorophenyl)urea
1-amidino-3-(2,4-dichlorophenyl)urea
1-amidino-3-(2,5-dichlorophenyl)urea
1-amidino-3-(2,6-dichlorophenyl)urea
1-amidino-3-(2-chloro-3-methylphenyl)urea
1-amidino-3-(2-chloro-4-methylphenyl)urea
1-amidino-3-(2-chloro-5-methylphenyl)urea
1-amidino-3-(2-chloro-5-fluorophenyl)urea
1-amidino-3-(2-chloro-5-bromophenyl)urea
1-amidino-3-(2-chloro-5-trifluoromethylphenyl)urea
1-amidino-3-(2-fluoro-5-chlorophenyl)urea
1-amidino-3-(2-chloro-6-fluorophenyl)urea
1-amidino-3-(2,6-difluorophenyl)urea
1-amidino-3-(2-methylphenyl)urea
1-amidino-3-(2-ethylphenyl)urea
1-amidino-3-(2-propylphenyl)urea
1-amidino-3-(4-trifluoromethoxyphenyl)urea
1-amidino-3-(4-methylsulfonylphenyl)urea
1-amidino-3-(4-trifluoromethylphenyl)urea
1-amidino-3-(3,4-dimethoxyphenyl)urea
1-amidino-3-(3,4,5-trimethoxyphenyl)urea
1-amidino-3-(3,4-diacetyloxyphenyl)urea
1-amidino-3-(3,4-dibenzyloxyphenyl)urea
1-amidino-3-(3,4,5-tribenzyloxyphenyl)urea
1-amidino-3-(3,4-diethoxyphenyl)urea
1-amidino-3-(2,4-dimethylphenyl)urea
1-amidino-3-(2,4-diethylphenyl)urea
1-amidino-3-(2-methyl-4-ethylphenyl)urea
1-amidino-3-(2-ethyl-4-methylphenyl)urea
1-amidino-3-(2-methyl-4-chlorophenyl)urea
1-amidino-3-(2-methyl-4-bromophenyl)urea
1-amidino-3-(2-methyl-4-fluorophenyl)urea
1-amidino-3(2-ethyl-4-chlorophenyl)urea
1-amidino-3-(2-ethyl-4-fluorophenyl)urea
1-amidino-3-(2-methyl-4-methoxyphenyl)urea
1-amidino-3-(2-ethyl-4-methoxyphenyl)urea
1-amidino-3-(2,4,6-trimethylphenyl)urea
1-amidino-3-(2,4-dimethyl-6-ethylphenyl)urea
1-amidino-3-(2,4-dimethyl-6-chlorophenyl)urea
1-amidino-3-(2,4-dimethyl-6-bromophenyl)urea
1-amidino-3-(2,4-dimethyl-6-fluorophenyl)urea
1-amidino-3-(2,4-dimethyl-6-trifluoromethylphenyl)urea
1-amidino-3-(2,4-dimethyl-6-nitrophenyl)urea
1-amidino-3-(2,4-dimethyl-6-methoxyphenyl)urea
1-amidino-3-(2,6-dimethyl-4-ethylphenyl)urea
1-amidino-3-(2,6-dimethyl-4-chlorophenyl)urea 1-amidino-3-(2,6-dimethyl-4-bromophenyl)urea
1-amidino-3-(2,6-dimethyl-4-fluorophenyl)urea
1-amidino-3-(2,6-dimethyl-4-methoxyphenyl)urea
1-amidino-3-(2-methyl-4,6-dichlorophenyl)urea
1-amidino-3-(2-methyl-4,6-difluorophenyl)urea
1-amidino-3-(2-methyl-4-fluoro-6-bromophenyl)urea
1-amidino-3-(2-methyl-4-fluoro-6-chlorophenyl)urea
1-amidino-3-(2-methyl-4-bromo-6-chlorophenyl)urea
1-amidino-3-(2-methyl-4-chloro-6-fluorophenyl)urea
1-amidino-3-(2-methyl-4-chloro-6-bromophenyl)urea
1-amidino-3-(2-methyl-4-methoxy-6-chlorophenyl)urea
1-amidino-3-(2-methyl-4-ethyl-6-chlorophenyl)urea
1-amidino-3-(2-methyl-4-chloro-6-trifluoromethylphenyl)urea
1-amidino-3-(2-methyl-4-trifluoromethyl-6-chlorophenyl)urea
1-amidino-3-(2-ethyl-4,6-dichlorophenyl)urea
1-amidino-3-(2-ethyl-4,6-difluorophenyl)urea
1-amidino-3-(2-ethyl-4-fluoro-6-bromophenyl)urea
1-amidino-3-(2-ethyl-4-fluoro-6-chlorophenyl)urea
1-amidino-3-(2-ethyl-4-bromo-6-chlorophenyl)urea
1-amidino-3-(2-ethyl-4-chloro-6-fluorophenyl)urea
1-amidino-3-(2-ethyl-4-chloro-6-bromophenyl)urea
1-amidino-3-(2,6-diethyl-4-chlorophenyl)urea
1-amidino-3-(2,6-diethyl-4-bromophenyl)urea
1-amidino-3-(2,6-diethyl-4-fluorophenyl)urea
1-amidino-3-(2,4-dimethyl-6-nitrophenyl)urea Hydrogenation of the 1-amidino-3-(3,4-diacetyloxyphenyl)urea and 1-amidino-3-(3,4-dibenzyloxyphenyl)urea with Pd/C in ethanol results in 1-amidino-3-(3,4-dihydroxyphenyl)urea. Hydrogenation of 1-amidino-3-(3,4,5-tribenzyloxyphenyl)urea with Pd/C in ethanol results in 1-amidino-3-(3,4,5-trihydroxyphenyl)urea.

EXAMPLE 2

1-Amidino-3-(2-methyl-4,6-dichlorophenyl)-3-methylurea

To 19.0 g. (0.1 mole) of 2,4-dichloro-6,N-dimethylaniline in 300 ml. of anhydrous benzene is added 325 ml. of 12.5% phosgene in benzene (0.40 mole). The reaction mixture is refluxed for 2 hours and the benzene removed under reduced pressure to also eliminate any excess phosgene. The residue is 2,4-dichloro-6,N-dimethylaniline acid chloride. This is then dissolved in 50 ml. of tetrahydrofuran and added dropwise to a heterogeneous mixture of 11.2 g. of potassium hydroxide and 18 g. of guanidine carbonate in 250 ml. of tetrahydrofuran. The mixture is stirred for about 10 hours, acidified with conc. hydrochloric acid and then basified with conc. sodium hydroxide solution while maintaining the mixture in an ice bath. This is then poured into 1500 ml. of water and the THF removed under diminished pressure. The mixture is extracted with ether, which is then dried and evaporated to dryness to obtain 1-amidino-3-(2-methyl-4,6-dichlorophenyl)-3-methylurea.

The hydrochloride salt is prepared by dissolving the free base in methanol and adding methanolic HCl to form the salt. The addition of ether accelerates the precipitation of the salt which is filtered off to obtain 1-amidino-3-(2-methyl-4,6-dichlorophenyl)-3-methylurea hydrochloride.

EXAMPLE 3

1-Amidino-3-(2-chloro-6-methylphenyl)urea

A quantity of 20 g. of 1-(2-chloro-6-methylphenyl)biguanide is added to 200 ml. of 10% hydrochloric acid and the mixture is refluxed for 3 hours. The reaction mixture is then filtered hot and then chilled. The material which separates is then filtered off and recrystallized from isopropanol/water to obtain 1-amidino-3-(2-chloro-6-methylphenyl)urea hydrochloride.

The free base is prepared by dissolving the salt in 200 ml. of water and adding a 10% sodium hydroxide solution until alkaline. The reaction mixture is then extracted with chloroform which is dried and evaporated to dryness to obtain 1-amidino-3-(2-chloro-6-methylphenyl)urea.

When the biguanides of Table I, below, are used in the above example in place of 1-(2-chloro-6-methylphenyl)biguanide, then the corresponding product of Table II is obtained.

Table I 1-(2,6-dimethylphenyl)biguanide
1-(2,6-diethylphenyl)biguanide
1-(2-methyl-6-methoxyphenyl)biguanide
1-(2,5-dichlorophenyl)biguanide
1-(2-methyl-6-chlorophenyl)biguanide
1-(2-methylphenyl)biguanide
1-(2-chloro-6-fluorophenyl)biguanide
1-(2-methyl-6-ethylphenyl)biguanide
1-(2,4,6-trimethylphenyl)biguanide
1-(2-methyl-4-bromo-6-chlorophenyl)biguanide
1-(3,4-dibenzyloxyphenyl)biguanide
1-(3,4,5-tribenzyloxyphenyl)biguanide
1-(3,4-dibenzyloxyphenyl)-5-methylbiguanide
1-(3,4-dibenzyloxyphenyl)-5,5-dimethylbiguanide
1-(3,4-dibenzyloxyphenyl)-4,5-dimethylbiguanide
1-(3,4-dibenzyloxyphenyl)-3-methylbiguanide
1-(3,4-dibenzyloxyphenyl)-1-methylbiguanide
1-(3,4-dibenzyloxyphenyl)-1,5-dimethylbiguanide
1-(3,4,5-triacetyloxyphenyl)biguanide
1-(3,4,5-tribenzyloxyphenyl)-5-methylbiguanide
1-(3,4,5-tribenzyloxyphenyl)-5,5-dimethylbiguanide
1-(3,4,5-tribenzyloxyphenyl)-4,5-dimethylbiguanide
1-(3,4,5-tribenzyloxyphenyl)-3-methylbiguanide
1-(3,4,5-tribenzyloxyphenyl)-1-methylbiguanide
1-(3,4,5-tribenzyloxyphenyl)-1,5-dimethylbiguanide
1-(2,6-dimethylphenyl)-5-methylbiguanide
1-(2,6-dimethylphenyl)-5,5-dimethylbiguanide
1-(2,6-dimethylphenyl)-4,5-dimethylbiguanide
1-(2,6-dimethylphenyl)-4,5,5-trimethylbiguanide
1-(2,6-dimethylphenyl)-3-methylbiguanide
1-(2,6-dimethylphenyl)-1-methylbiguanide
1(2,6-dimethylphenyl)-1,3-dimethylbiguanide
1-(2,6-dimethylphenyl)-3,5-dimethylbiguanide
1-(2,6-dimethylphenyl)-3,5,5-trimethylbiguanide
1-(2,6-dimethylphenyl)-3,4,5-trimethylbiguanide
1-(2,6-dimethylphenyl)-1,5-dimethylbiguanide
1-(2,6-dimethylphenyl)-1,3,5-trimethylbiguanide
1-(2,6-dimethylphenyl)-1,3,5,5-tetramethylbiguanide
1-(2,6-dimethylphenyl)-1,3,4,5-tetramethylbiguanide
1-(2,6-dimethylphenyl)-1,3,4,5,5-pentamethylbiguanide
1-(2,6-diethylphenyl-5-methylbiguanide
1-(2-methyl-6-methoxyphenyl)-5-methylbiguanide
1-(2-methyl-6-chlorophenyl)-5-methylbiguanide
1-(2-methyl-6-ethylphenyl)-5-methylbiguanide
1-(2-methylphenyl)-5-methylbiguanide
1-(2,4,6-trimethylphenyl)-5-methylbiguanide
1-(2-methyl-4-bromo-6-chlorophenyl)-5-methylbiguanide
1-(2-chloro-6-fluorophenyl)-5-methylbiguanide
1-(2,5-dichlorophenyl)-5-methylbiguanide 1-(2-chloro-6-bromophenyl)-5-methylbiguanide
1-(2-chloro-5-bromophenyl)-5-methylbiguanide
1-(2-chloro-5-fluorophenyl)-5-methylbiguanide
1-(2-fluoro-5-chlorophenyl)-5-methylbiguanide
1-(2-fluoro-5-bromophenyl)-5-methylbiguanide
1-(2,4,6-triethylphenyl)-5-methylbiguanide
1-(2,4-dimethyl-6-ethylphenyl)-5-methylbiguanide
1-(2,6-dimethyl-4-ethylphenyl)-5-methylbiguanide
1-(2-ethyl-6-chlorophenyl)-5-methylbiguanide
1-(2-ethylphenyl)-5-methylbiguanide
1-(2-ethyl-4-bromo-6-chlorophenyl)-5-methylbiguanide
1-(2-ethyl-6-methoxyphenyl)-5-methylbiguanide
1-(2-methyl-6-ethoxyphenyl)-5-methylbiguanide
1-methyl-1-(2,6-diethylphenyl)biguanide
1-methyl-1-(2-methyl-6-methoxyphenyl)biguanide
1-methyl-1-(2-methyl-6-chlorophenyl)biguanide
1-methyl-1-(2-methyl-6-ethylphenyl)biguanide
1-methyl-1-(2-methylphenyl)biguanide
1-methyl-1-(2,4,6-trimethylphenyl)biguanide
1-methyl-1-(2-methyl-4-bromo-6-chlorophenyl)biguanide
1-methyl-1-(2-chloro-6-fluorophenyl)biguanide
1-methyl-1-(2,5-dichlorophenyl)biguanide
1-(2,6-diethylphenyl)-3-methylbiguanide
1-(2-methyl-6-methoxyphenyl)-3-methylbiguanide
1-(2-methyl-6-chlorophenyl)-3-methylbiguanide
1-(2-methyl-6-ethylphenyl)-3-methylbiguanide
1-(2-methylphenyl)-3-methylbiguanide
1-(2,4,6-trimethylphenyl)-3-methylbiguanide
1-(2-methyl-4-bromo-6-chlorophenyl)-3-methylbiguanide
1-(2-chloro-6-fluorophenyl)-3-methylbiguanide
1-(2,5-dichlorophenyl)-3-methylbiguanide
1-(2,6-dimethylphenyl)-5-ethylbiguanide
1-(2,6-dimethylphenyl)-5-propylbiguanide
1-(2,6-dimethylphenyl)-5-i-propylbiguanide
1-(2,6-dimethylphenyl)-5-butylbiguanide
1-(2,6-dimethylphenyl)-5-i-butylbiguanide
1-(2,6-dimethylphenyl)-5-sec-butylbiguanide
1-(2,6-dimethylphenyl)-5-t-butylbiguanide
1-(2,6-dimethylphenyl)-5-pentylbiguanide
1-(2,6-dimethylphenyl)-5-hexylbiguanide
1-(2,6-dimethylphenyl)-5-heptylbiguanide
1-(2,6-dimethylphenyl)-5-cyclopropylbiguanide
1-(2,6-dimethylphenyl)-5-cyclobutylbiguanide
1-(2,6-dimethylphenyl)-5-cyclopentylbiguanide
1-(2,6-dimethylphenyl)-5-cyclohexylbiguanide
1-(2,6-dimethylphenyl)-5-phenylbiguanide
1-(2,6-dimethylphenyl)-5-benzylbiguanide
1-(2,6-dimethylphenyl)-5-phenethylbiguanide
1-(2,6-dimethylphenyl)-5-(2,6-dimethylphenyl)biguanide
1-(2,6-dimethylphenyl)-5-(2-methylphenyl)biguanide
1-(2,6-dimethylphenyl)-5-(2,6-diethylphenyl)biguanide
1-(2,6-dimethylphenyl)-5-(2-methyl-6-chlorophenyl)biguanide
1-(2,6-dimethylphenyl)-5-(2,4,6-trimethylphenyl)biguanide
1-(2,6-dimethylphenyl)-5,5-pentamethylenebiguanide)biguanide
1-(2,6-dimethylphenyl)-5,5-(N-methyl-3'-azapentamethylene)biguanide
1-(2,6-dimethylphenyl)-5,5-(N-methyl-3'-azaheptamethylene)biguanide
1-(2,6-dimethylphenyl)-5,5-(3'-oxopentamethylene)biguanide
1-(2,6-dimethylphenyl)-5,5-(2'-thiatetramethylene)biguanide
1-(2,6-dimethylphenyl)-5-methyl-5-ethylbiguanide
1-(2,6-dimethylphenyl)-5,5-diethylbiguanide
1-(2,6-dimethylphenyl)-5-methyl-5-benzylbiguanide
1-(2,6-dimethylphenyl)-5,5-dibenzylbiguanide

TABLE II 1-amidino-3-(2,6-dimethylphenyl)urea
1-amidino-3-(2,6-diethylphenyl)urea
1-amidino-3-(2-methyl-6-methoxyphenyl)urea
1-amidino-3-(2,5-dichlorophenyl)urea
1-amidino-3-(2-methyl-6-chlorophenyl)urea
1-amidino-3-(2-methylphenyl)urea
1-amidino-3-(2-chloro-6-fluorophenyl)urea
1-amidino-3-(2-methyl-6-ethylphenyl)urea
1-amidino-3-(2,4,6-trimethylphenyl)urea
1-amidino-3-(2-methyl-4-bromo-6-chlorophenyl)urea
1-amidino-3-(3,4-dibenzyloxyphenyl)urea
1-amidino-3-(3,4-dihydroxyphenyl)urea
1-amidino-3-(3,4,5-tribenzyloxyphenyl)urea
1-amidino-3-(3,4,5-trihydroxyphenyl)urea
1-(N-methylamidino)-3-(3,4-dihydroxyphenyl)urea
1-(N,N-dimethylamidino)-3-(3,4-dihydroxyphenyl)urea
1-(N,N'-dimethylamidino)-3-(3,4-dihydroxyphenyl)urea
1-methyl-1-amidino-3-(3,4-dihydroxyphenyl)urea
3-methyl-1-amidino-3-(3,4-dihydroxyphenyl)urea
1-methyl-1-(N-methylamidino)-3-(3,4-dihydroxyphenyl)urea
1-amidino-3-(3,4,5-trihydroxyphenyl)urea
1-(N-methylamidino)-3-(3,4,5-trihydroxyphenyl)urea
1-(N,N-dimethylamidino)-3-(3,4,5-trihydroxyphenyl)urea
1-(N,N'-dimethylamidino)-3-(3,4,5-trihydroxyphenyl)urea
1-methyl-1-amidino-3-(3,4,5-trihydroxyphenyl)urea
3-methyl-1-amidino-3-(3,4,5-trihydroxyphenyl)urea
1-methyl-1-(N-methylamidino)-3-(3,4,5-trihydroxyphenyl)urea
1-(N-methylamidino)-3-(2,6-dimethylphenyl)urea
1-(N,N-dimethylamidino)-3-(2,6-dimethylphenyl)urea
1-(N,N'-dimethylamidino)-3-(2,6-dimethylphenyl)urea
1-(N,N,N'-trimethylamidino)-3-(2,6-dimethylphenyl)urea
1-methyl-1-amidino-3-(2,6-dimethylphenyl)urea
3-methyl-1-amidino-3-(2,6-dimethylphenyl)urea
1,3-dimethyl-1-amidino-3-(2,6-dimethylphenyl)urea
1-methyl-1-(N-methylamidino)-3-(2,6-dimethylphenyl)urea
1-methyl-1-(N,N-dimethylamidino)-3-(2,6-dimethylphenyl)urea
1-methyl-1-(N,N'-dimethylamidino)-3-(2,6-dimethylphenyl)urea
3-methyl-1-(N-methylamidino)-3-(2,6-dimethylphenyl)urea
1,3-dimethyl-1-(N-methylamidino)-3-(2,6-dimethylphenyl)urea
1,3-dimethyl-1-(N,N-dimethylamidino)-3-(2,6-dimethylphenyl)urea
1,3-dimethyl-1-(N,N'-dimethylamidino)-3-(2,6-dimethylphenyl)urea
1,3-dimethyl-1-(N,N,N'-trimethylamidino)-3-(2,6-dimethylphenyl)urea
1-(N-methylamidino)-3-(2,6-diethylphenyl)urea 1-(N-methylamidino)-3-(2-methyl-6-methoxyphenyl)urea
1-(N-methylamidino)-3-(2-methyl-6-chlorophenyl)urea
1-(N-methylamidino)-3-(2-methyl-6-ethylphenyl)urea
1-(N-methylamidino)-3-(2-methylphenyl)urea
1-(N-methylamidino)-3-(2,4,6-trimethylphenyl)urea
1-(N-methylamidino)-3-(2-methyl-4-bromo-6-chlorophenyl)urea
1-(N-methylamidino)-3-(2-chloro-6-fluorophenyl)urea
1-(N-methylamidino)-3-(2,5-dichlorophenyl)urea
1-(N-methylamidino)-3-(2-chloro-6-bromophenyl)urea
1-(N-methylamidino)-3-(2-chloro-5-bromophenyl)urea
1-(N-methylamidino)-3-(2-chloro-5-fluorophenyl)urea
1-(N-methylamidino)-3-(2-fluoro-5-chlorophenyl)urea
1-(N-methylamidino)-3-(2-fluoro-5-bromophenyl)urea
1-(N-methylamidino)-3-(2,4,6-triethylphenyl)urea
1-(N-methylamidino)-3-(2,4-dimethyl-6-ethylphenyl)urea
1-(N-methylamidino)-3-(2,6-dimethyl-4-ethylphenyl)urea
1-(N-methylamidino)-3-(2-ethyl-6-chlorophenyl)urea
1-(N-methylamidino)-3-(2-ethylphenyl)urea
1-(N-methylamidino)-3-(2-ethyl-4-bromo-6-chlorophenyl)urea
1-(N-methylamidino)-3-(2-ethyl-6-methoxyphenyl)urea
1-(N-methylamidino)-3-(2-methyl-6-ethoxyphenyl)urea
1-amidino-3-methyl-3-(2,6-diethylphenyl)urea
1-amidino-3-methyl-3-(2-methyl-6-methoxyphenyl)urea
1-amidino-3-methyl-3-(2-methyl-6-chlorophenyl)urea
1-amidino-3-methyl-3-(2-methyl-6-ethylphenyl)urea
1-amidino-3-methyl-3-(2-methylphenyl)urea
1-amidino-3-methyl-3-(2,4,6-trimethylphenyl)urea
1-amidino-3-methyl-3-(2-methyl-4-bromo-6-chlorophenyl)urea
1-amidino-3-methyl-3-(2-chloro-6-fluorophenyl)urea
1-amidino-3-methyl-3-(2,5-dichlorophenyl)urea
1-(methyl-1-amidino-3-(2,6-diethylphenyl)urea
1-(methyl-1-amidino-3-(2-methyl-6-methoxyphenyl)urea
1-(methyl-1-amidino-3-(2-methyl-6-chlorophenyl)urea
1-(methyl-1-amidino-3-(2-methyl-6-ethylphenyl)urea
1-(methyl-1-amidino-3-(2-methylphenyl)urea
1-(methyl-1-amidino-3-(2,4,6-trimethylphenyl)urea
1-(methyl-1-amidino-3-(2-methyl-4-bromo-6-chlorophenyl)urea
1-(methyl-1-amidino-3-(2-chloro-6-fluorophenyl)urea
1-(methyl-1-amidino-3-(2,5-dichlorophenyl)urea
1-(N-ethylamidino)-3-(2,6-dimethylphenyl)urea
1-(N-propylamidino)-3-(2,6-dimethylphenyl)urea
1-(N-i-propylamidino)-3-(2,6-dimethylphenyl)urea
1-(N-butylamidino)-3-(2,6-dimethylphenyl)urea
1-(N-i-butylamidino)-3-(2,6-dimethylphenyl)urea
1-(N-sec-butylamidino)-3-(2,6-dimethylphenyl)urea
1-(N-t-butylamidino)-3-(2,6-dimethylphenyl)urea
1-(N-pentylamidino)-3-(2,6-dimethylphenyl)urea
1-(N-hexylamidino)-3-(2,6-dimethylphenyl)urea
1-(N-heptylamidino)-3-(2,6-dimethylphenyl)urea
1-(N-cyclopropylamidino)-3-(2,6-dimethylphenyl)urea
1-(N-cyclobutylamidino)-3-(2,6-dimethylphenyl)urea
1-(N-cyclopentylamidino)-3-(2,6-dimethylphenyl)urea
1-(N-cyclohexylamidino)-3-(2,6-dimethylphenyl)urea
1-(N-phenylamidino)-3-(2,6-dimethylphenyl)urea
1-(N-benzylamidino)-3-(2,6-dimethylphenyl)urea
1-(N-phenethylamidino)-3-(2,6-dimethylphenyl)urea
1-[N-(2,6-dimethylphenyl)amidino]-3-(2,6-dimethylphenyl)urea
1-[N-(2-methylphenyl)amidino]-3-(2,6-dimethylphenyl)urea
1-[N-(2,6-diethylphenyl)amidino]-3-(2,6-dimethylphenyl)urea
1-[N-(2-methyl-6-chlorophenyl)amidino]-3-(2,6-dimethylphenyl)urea
1-[N-(2,4,6-trimethylphenyl)amidino]-3-(2,6-dimethylphenyl)urea
1-(N,N-pentamethyleneamidino)-3-(2,6-dimethylphenyl)urea
1-[(N,N-(N-methyl-3'-azapentamethylene)amidino]-3-(2,6-dimethylphenyl)urea
1-[N,N-(N-methyl-3'-azaheptamethylene)amidino]-3-(2,6-dimethylphenyl)urea
1-[N,N-(3'-oxopentamethylene)amidino]-3-(2,6-dimethylphenyl)urea
1-[N,N-(2'-thiatetramethylene)amidino]-3-(2,6-dimethylphenyl)urea
1-(N-methyl-N-ethylamidino)-3-(2,6-dimethylphenyl)urea
1-(N,N-diethylamidino)-3-(2,6-dimethylphenyl)urea
1-(N-methyl-N-benzylamidino)-3-(2,6-dimethylphenyl)urea
1-(N,N-dibenzylamidino)-3-(2,6-dimethylphenyl)urea

We claim:

1. A method for the treatment of diarrhea in humans and mammals which comprises the administering thereto between 0.01 to 500 mg/kg per day of a compound of the formula:

where:
$R_2$, $R_3$, $R_4$, $R_5$ and $R_6$ may be the same or different and are:
hydrogen,
halo,
loweralkyl,
trifluoromethyl,
nitro,
methoxy, ethoxy
hydroxy,
benzyloxy
acetyloxy,
cyano,
trifluoromethoxy or
methylsulfonyl
R and $R_n$ are hydrogen or loweralkyl;
R' and R" are hydrogen,
alkyl, cyclopropyl, cyclobutyl, cyclopentyl, cyclohexyl, benzyl or phenethyl; and
the non-toxic acid addition salts thereof.
2. The method of claim 1
where:
$R_2$, $R_3$, $R_4$, $R_5$ and $R_6$ are hydrogen,
halo,
loweralkyl,
trifluoromethyl,
nitro,
hydroxy
methoxy or
ethoxy; and R and $R_n$ are hydrogen or loweralkyl and R' and R'' are hydrogen or alkyl provided R, R' and R'' are not all hydrogen at the same time.
3. The method of claim 1
where:
$R_2$ is hydrogen or loweralkyl;
$R_3$ and $R_5$ are hydrogen, hydroxy or loweralkoxy;
$R_4$ is hydrogen,
loweralkyl,
hydroxy,
methoxy,
ethoxy or
halo;
$R_6$ is hydrogen,
loweralkyl,
nitro,
methoxy,
ethoxy or
halo.
R and $R_n$ are hydrogen or loweralkyl; and
R' and R'' are hydrogen or alkyl; provided R, R' and R'' are not all hydrogen at the same time.
4. The method of claim 1 where:
$R_2$ is hydrogen,
methyl or
ethyl;
$R_3$ is hydrogen,
hydroxy or
methoxy;
$R_4$ is hydrogen,
methyl,
ethyl,
hydroxy,
methoxy,
chloro or
bromo;
$R_5$ is hydrogen,
hydroxy or
methoxy;
$R_6$ is hydrogen,
methyl,
ethyl,
nitro,
methoxy,
ethoxy,
chloro,
bromo or
fluoro;
R and $R_n$ are hydrogen, methyl or ethyl; and
R' and R'' are hydrogen,
methyl,
ethyl,
propyl,
i-propyl,
butyl,
i-butyl,
sec-butyl,
t-butyl,
pentyl,
hexyl or;
heptyl; provided R, R' and R'' are not all hydrogen at the same time.
5. A method for the treatment of diarrhea in humans and mammals which comprises the administering thereto between 0.01 to 500 mg/kg per day of a compound of the formula:

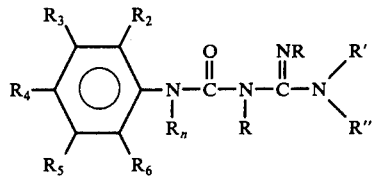

where substitution of $R_2$, $R_3$, $R_4$, $R_5$ and $R_6$ are selected from the group consisting of:
$R_2$ is loweralkyl;
$R_2$ and $R_6$ are loweralkyl;
$R_2$ is loweralkyl and $R_6$ is methoxy or ethoxy;
$R_2$ is loweralkyl and $R_6$ is halo;
$R_2$ is loweralkyl and $R_6$ is nitro;
$R_2$, $R_4$ and $R_6$ are loweralkyl; and
$R_2$ is loweralkyl and $R_4$ and $R_6$ are halo;
all other members of $R_2$, $R_3$, $R_4$, $R_5$, and $R_6$ being hydrogen;
R is hydrogen or loweralkyl;
R' and R'' are hydrogen,
alkyl,
cyclopropyl, cyclobutyl, cyclopentyl, cyclohexyl, benzyl or phenethyl;
$R_n$ is hydrogen or loweralkyl provided at least one of R, R' and R'' is other than hydrogen; and
the non-toxic acid addition salts thereof.
6. The method of claim 5 where:
$R_2$ is loweralkyl;
7. The method of claim 5 where:
$R_2$ and $R_6$ are loweralkyl;
8. The method of claim 5 where:
$R_2$ is loweralkyl and $R_6$ is methoxy or ethoxy;
9. The method of claim 5 where:
$R_2$ is loweralkyl and $R_6$ is halo;
10. The method of claim 5 where:
$R_2$ is loweralkyl and $R_6$ is nitro;
11. The method of claim 5 where:
$R_2$, $R_4$, and $R_6$ are loweralkyl; or
12. The method of claim 5 where:
$R_2$ is loweralkyl and $R_4$ and $R_6$ are halo.
13. The method of claim 3 where: p1 $R_3$ and $R_4$ are hydroxy, methoxy or ethoxy;
14. The method of claim 3 where:
$R_3$, $R_4$ and $R_5$ are hydroxy, methoxy or ethoxy;
15. The method of claim 3 where:
$R_2$ and $R_5$ are halo; or
16. The method of claim 3 where:
$R_2$ and $R_6$ are halo.
17. The method of claim 3 where:
R, R' and R'' are hydrogen or lowerlakyl provided all are not hydrogen at the same time.
18. The method of claim 3 where:
R and R' are hydrogen or loweralkyl and R'' is an alkyl group from 3 to 7 atoms.
19. The method of claim 7 wherein said compound is 1-(N-methylamidino)-3-(2,6-dimethylphenyl)urea.

20. The method of claim 7 wherein said compound is 1-(N-methylamidino)-3-(2,6-diethylphenyl)urea.

21. The method of claim 7 wherein said compound 1-(N-methylamidino)-3-(2-methyl-6-ethylphenyl-)urea.

22. A method for the treatment of diarrhea in humans and mammals which comprises the administering thereto between 0.01 and 500 mg/kg per day of a compound of the formula:

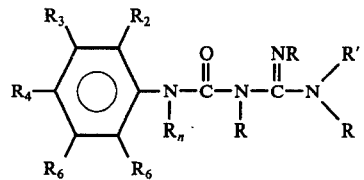

where substitution of $R_2$, $R_3$, $R_4$, $R_5$ and $R_6$ are selected from the group consisting of:
- $R_3$ and $R_4$ are hydroxy, methoxy or ethoxy;
- $R_3$, $R_4$ and $R_5$ are hydroxy, methoxy or ethoxy;
- $R_2$ and $R_5$ are dihalo; and
- $R_2$ and $R_6$ are dihalo;
- all other members of $R_2$, $R_3$, $R_4$, $R_5$ and $R_6$ being hydrogen; R is hydrogen or loweralkyl;
- R' and R" are hydrogen, alkyl, cyclopropyl, cyclobutyl, cyclopentyl, cyclohexyl, benzyl or phenethyl;
- $R_n$ is hydrogen or loweralkyl provided at least one of R, R' and R" is other than hydrogen; and
- the non-toxic acid addition salts thereof.

* * * * *